US00PP21558P3

(12) United States Plant Patent
Chandler

(10) Patent No.: US PP21,558 P3
(45) Date of Patent: Dec. 7, 2010

(54) 'WINTER DAWN' STRAWBERRY PLANT

(50) Latin Name: *Fragaria×ananassa*
Varietal Denomination: Winter Dawn

(75) Inventor: Craig K. Chandler, Dover, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 1577 days.

(21) Appl. No.: 11/093,191

(22) Filed: Jun. 13, 2005

(65) Prior Publication Data

US 2009/0013438 P1 Jan. 8, 2009

(51) Int. Cl.
*A01H 5/00* (2006.01)

(52) U.S. Cl. ..... Plt./208

(58) Field of Classification Search ..... Plt./208
See application file for complete search history.

*Primary Examiner*—Annette H Para
(74) *Attorney, Agent, or Firm*—Jondle & Associates, P.C.

(57) ABSTRACT

A new and distinct variety of strawberry (*Fragaria×ananassa*), which originated from seed produced by a hand-pollinated cross between FL 93-103 and FL 95-316. The new strawberry, named 'Winter Dawn', is distinguished by high November through February production of fruit that are medium to large in size and moderately resistant to Botrytis and anthracnose fruit rot diseases when grown in Dover, Fla. or other areas that have a subtropical climate similar to that of Dover.

2 Drawing Sheets

Botanical designation: *Fragaria×ananassa* Duchesne

BACKGROUND OF THE NEW VARIETY

The present invention relates to a new and distinct variety of strawberry (*Fragaria×ananassa* Duchesne) plant that is named 'Winter Dawn' and more particularly to a strawberry plant that is distinguished by its high fruit yield during the winter in west central Florida, as well as its ability to produce medium to large, easily harvestable fruit. Asexual propagation was performed at Dover, Fla. where the selection was made and plants were tested. Contrast is made to 'Strawberry Festival' (U.S. plant Pat. No. 14,739), currently the dominant variety in Hillsborough County, Fla., for reliable description. This new variety is a promising candidate for commercial success because it produces high fruit yields during a desirable market window. Also, because of its Colletotrichum crown rot resistance, it can be successfully propagated in Florida, giving Florida growers the option of propagating their own plants.

ORIGIN OF THE VARIETY

This strawberry plant (genotype) originated in a strawberry breeding plot at Dover, Fla. The seed parent was FL 93-103, and the pollen parent was FL 95-316, both non-patented University of Florida breeding selections. The seeds resulting from the controlled hybridization were germinated in a greenhouse and the resulting seedlings were planted and allowed to produce daughter plants by asexual propagation (i.e. by runners). Two daughter plants from each seedling were transplanted to raised beds, where they fruited. 'Winter Dawn' strawberry (as represented by two daughter plants from the original seedling) exhibited attractive fruit, and therefore was selected for further evaluation. 'Winter Dawn' was selected from among 143 sibling genotypes as the 39th selection of the 1997-98 season, and thus was designated FL 97-39. It has been asexually propagated by runners, annually, and further test plantings have established that the vegetative and fruit characteristics of the propagules are identical to the initial two daughter plants.

SUMMARY OF THE VARIETY

'Winter Dawn', when grown in a subtropical fall and winter climate, is set apart from all other strawberry plants by a combination of the following characteristics: resistance to Colletotrichum crown rot (caused by *C. gloeosporioides*); ability to produce large fruit on a relatively small plant; high November through February yield (greater than 500 grams of fruit per plant); fruit that are moderately resistant to Botrytis and anthracnose fruit rot diseases.

BRIEF DESCRIPTION OF THE DRAWING

The accompanying photographs show a typical specimen of the plant and fruit as seen in early January and early March.

DETAILED BOTANICAL DESCRIPTION

The following botanical description is that of mature plants of the variety grown under the ecological conditions (warm days, cool nights) prevailing at Dover, Fla. in mid December. Colors are described using the Pantone® Color Formula Guide.

'Winter Dawn' is a short day cultivar. It produces numerous runners (stolons) in the summer nursery, but relatively few runners after being transplanted to the fruiting field. Average height and width for mature plants is 17 cm and 26 cm respectively. Average petiole length and diameter is 12.7 cm and 2.5 mm respectively, and petioles have a medium pubescence. Average length and breadth of terminal leaflets is 83 and 67 mm respectively. Average length and breadth of secondary leaflets is 74 and 67 mm respectively. Leaflet margins are crenate and average 17 serrations per terminal leaflet, and 17 per secondary leaflet. The upper leaf surface is a dark grey green (Pantone® 364 U); the lower leaf surface is a light grey green (Pantone® 577 U); and the petiole is a medium yellow green (Pantone® 390 U). Flowers open below the canopy, and have an average of 6 petals and 24 stamens. Individual petals have a length and width of 13 mm. The diameter of the corolla (i.e. the petals collectively) is 35 mm. The color of the calyx is yellow green (Pantone® 363 U). Pedicels attached to mature primary fruit are 6.8 to 8.0 cm long, with secondary pedicels generally branching from the peduncle within 20 mm of the crown. Mean fruit weight is greater than or equal to that of 'Strawberry Festival' (Table 1 and 2). Primary fruit are medium conic to wedge shaped (weighing 25-40 g); whereas secondary and tertiary fruit are mostly short conic to oval (weighing 10-25 g). Often fruit of 'Winter Dawn' are asymetrical, but still marketable. The external color of fully mature fruit is mostly deep red (Pantone® 1807C) and glossy, but is an orange red (Pantone® 1797C) in the achene depressions and around the calyx. Internal color is a warm red (Pantone® 1795C) fading into white. The achenes are generally greenish yellow to medium red and level with or slightly protruding from the fruit surface. The calyx is generally medium in size and attractive. Fruit of 'Winter Dawn' are as firm or less firm than those of 'Strawberry Festival' (Tables 3 and 4). The flavor of this fruit is slightly acidic with moderate aroma, and not as highly regarded as that of 'Strawberry Festival' (Table 4). The preferred planting date for 'Winter Dawn' is September 20 to October 5. 'Winter Dawn' had higher December through February yields than 'Strawberry Festival' in trials during the 2001-02 and 2002-03 seasons (Table 1 and 2). 'Winter Dawn' is moderately resistant to the two most serious disease problems on strawberry in Florida: Botrytis fruit rot (caused by *Botrytis cinerea* Pers.exFr.) and anthracnose fruit rot (caused by *Colletotrichum acutatum Simmonds*). In an unsprayed trial during the 2001-02 and 2002-03 seasons, 8.8 and 4.0% of the 'Winter Dawn' fruit harvested from 19 Feb. to 15 Mar. showed symptoms of Botrytis fruit rot, compared to 18.7 and 6.7% for 'Sweet Charlie' (U.S. plant Pat. No. 8,729), the susceptible control. In another unsprayed trial during the 2001-02 and 2002-03 seasons, 3.3 and 14.1% of the Winter Dawn' fruit harvested from 19 Feb. to 22 Mar. showed symptoms of anthracnose fruit rot, compared to 28.9 and 46.9% for 'Strawberry Festival', the susceptible control. The susceptibility of 'Winter Dawn' to the twospotted spider mite (*Tetranychus urtricae* Koch) is unknown, but a serious infestation has not yet been observed in research center or commercial trials.

TABLE 1

Performance of strawberry cultivars at Dover, Fla. during the 2001-02 season.

| | Marketable yield (g/plant) | | | | |
|---|---|---|---|---|---|
| Cultivar | November/ December | January | February | Total | Wt/fruit[z] (g) |
| Winter Dawn | 219 a[y] | 118 ab | 232 a | 570 a | 18.2 b |
| S. Festival | 151 b | 140 ab | 212 ab | 503 b | 16.5 c |
| Carmine | 180 ab | 108 b | 164 b | 457 b | 16.8 bc |
| S. Charlie | 82 c | 171 a | 204 ab | 457 b | 17.0 bc |
| Earlibrite | 177 b | 146 ab | 168 b | 491 b | 20.1 a |

[z]Mean fruit weight was determined by dividing total marketable fruit yield per plot by total marketable fruit number per plot.
[y]Means based on four replications. Mean separation within columns by Fisher's protected LSD test, P ≦ 0.05.

TABLE 2

Performance of strawberry cultivars at Dover, Fla. during the 2002-03 season.

| | Marketable yield (g/plant) | | | | |
|---|---|---|---|---|---|
| Cultivar | December | January | February | Total | Wt/ fruit[z] (g) |
| Winter Dawn | 67[y] c | 103 a | 466 a | 635 a | 22.4 ab |
| S. Festival | 82 bc | 19 c | 259 b | 359 bc | 23.4 a |
| Carmine | 102 a | 32 bc | 282 b | 416 b | 20.6 bc |
| Earlibrite | 107 a | 61 b | 156 c | 324 c | 24.5 a |
| Sweet Charlie | 90 ab | 46 bc | 284 b | 420 b | 19.4 c |

[z]Mean fruit weight was determined by dividing total marketable fruit yield per plot by total marketable fruit number per plot.
[y]Means based on four replications. Mean separation within columns by Fisher's protected LSD test, P ≦ 0.05.

TABLE 3

Physical and chemical characteristics of strawberry fruit harvested at Dover, Fla. Feb. 18, 2004 and Mar. 22, 2004[z].

| | L value[y] | | Firmness (kg force) | |
|---|---|---|---|---|
| Cultivar | February | March | February | March |
| Winter Dawn | 37.0 a | 35.8 a | 0.39 a | 0.33 b |
| S. Festival | 33.6 b | 34.5 ab | 0.48 a | 0.55 a |
| Treasure | 32.6 b | — | 0.43 a | — |
| Sweet Charlie | 36.9 a | — | 0.24 b | — |
| Camarosa | — | 34.8 ab | | 0.49 a |
| Camino Real | | 33.1 b | | 0.50 a |

| | Soluble solids (%) | | Titratable acidity (% citric acid) | |
|---|---|---|---|---|
| Cultivar | February | March | February | March |
| Winter Dawn | 5.7 b | 6.3 ab | 0.90 a | 0.64 b |
| S. Festival | 7.0 a | 6.7 a | 0.88 a | 0.74 a |
| Treasure | 6.7 a | — | 0.85 a | — |
| Sweet Charlie | 5.7 b | — | 0.55 b | — |
| Camarosa | | 6.4 ab | | 0.79 a |
| Camino Real | | 6.2 b | | 0.73 a |

[z]L and firmness values are the average of 10 observations. Mean separation within columns by Duncan's multiple range test, P ≦ 0.05.
[y]The lower the value, the darker the color.

TABLE 4

Sensory characteristics of strawberry fruit harvested at Dover, Fla. Feb. 18, 2004 and Mar. 22 2004[z].

| | Firmness | | Flavor | |
|---|---|---|---|---|
| Cultivar | February | March | February | March |
| Winter Dawn | 7.0 a | 6.4 b | 5.6 b | 6.8 a |
| S. Festival | 6.9 a | 6.8 ab | 6.6 a | 6.5 a |
| Treasure | 7.0 a | — | 7.1 a | — |
| Sweet Charlie | 5.7 b | — | 5.7 b | — |
| Camarosa | — | 6.4 b | | 6.5 a |
| Camino Real | | 7.2 a | | 6.7 a |

| | Sweetness | | Overall acceptability | |
|---|---|---|---|---|
| Cultivar | February | March | February | March |
| Winter Dawn | 5.2 c | 6.4 a | 5.7 b | 6.5 a |
| S. Festival | 6.1 ab | 6.3 a | 6.7 a | 6.7 a |

TABLE 4-continued

Sensory characteristics of strawberry fruit harvested at Dover, Fla. Feb. 18, 2004 and Mar. 22 2004[z].

| | | | | |
|---|---|---|---|---|
| Treasure | 6.4 a | — | 7.1 a | — |
| Sweet Charlie | 5.6 bc | — | 5.9 b | — |
| Camarosa | | 6.2 a | | 6.6 a |
| Camino Real | | 6.4 a | | 6.7 a |

[z]Means based on the ratings of 72 untrained panelists. Mean separation within columns by Tukey's procedure $P \leqq 0.05$. Characteristics are rated on a 1-9 hedonic scale, with 1 = dislike extremely, 5 = neither like nor dislike, and 9 = like extremely.

We claim:

1. A new and distinct strawberry plant as illustrated and described, characterized by 1) moderate resistance to *Colletotrichum* crown rot and *Botrytis* and anthracnose fruit rot diseases, and 2) high November through February production of medium to large fruit, when grown in the Dover/Plant City are of Fla.

* * * * *

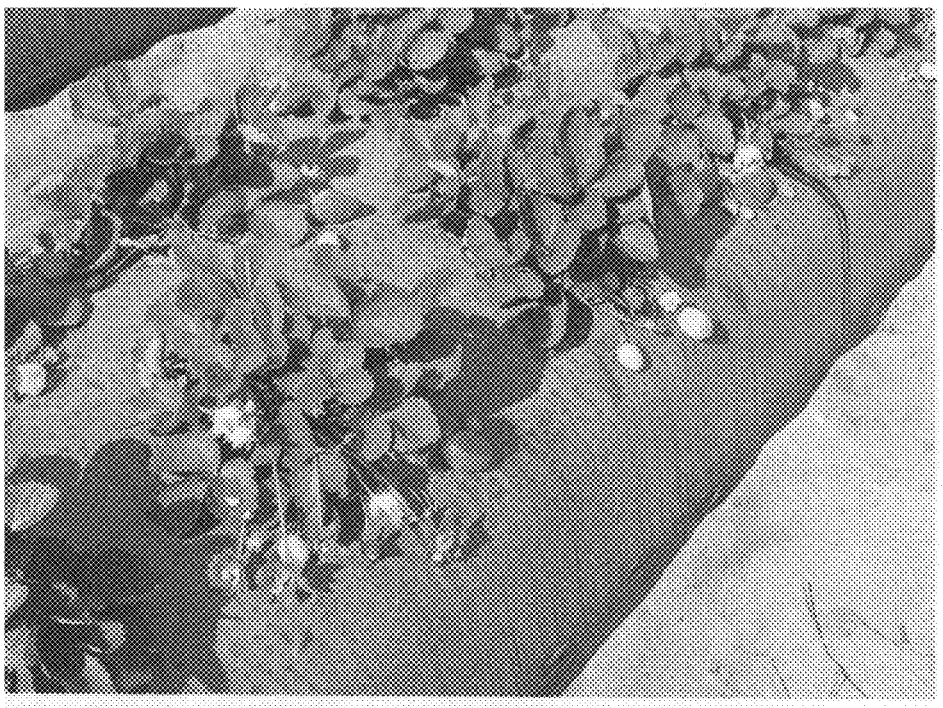
'Winter Dawn' strawberry, 1-6-04
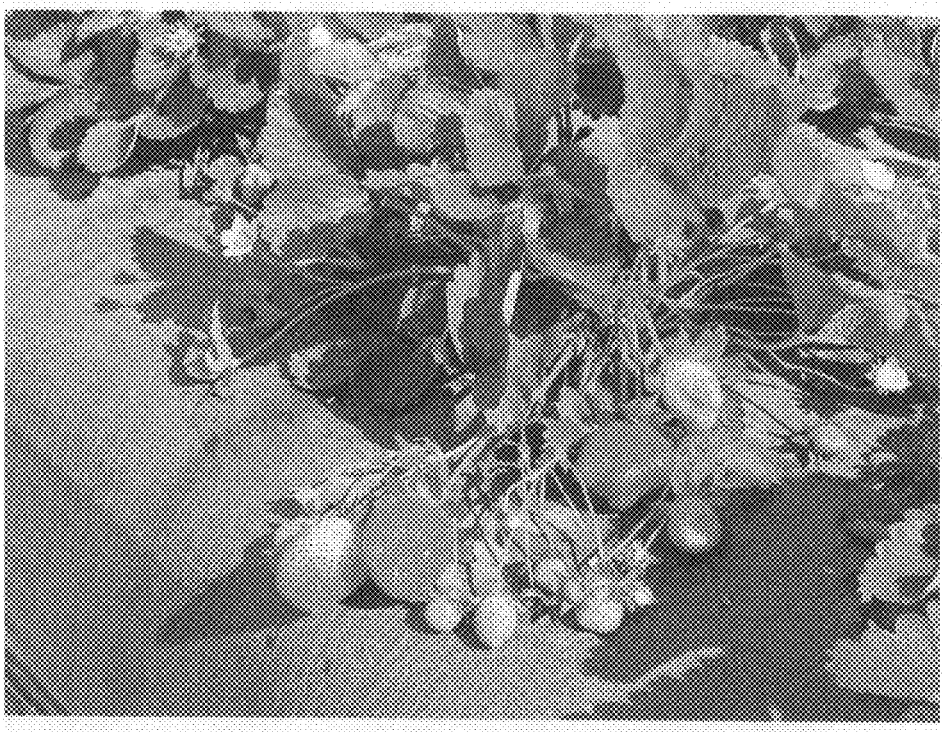
'Winter Dawn' strawberry, 1-6-04

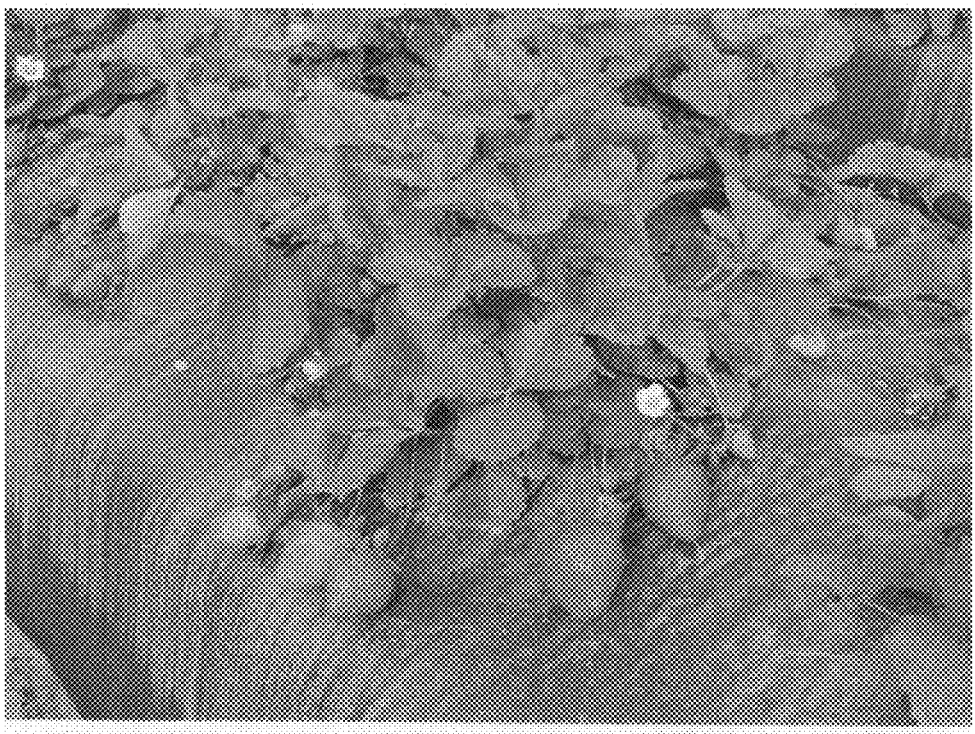
'Winter Dawn' strawberry, 3-6-02
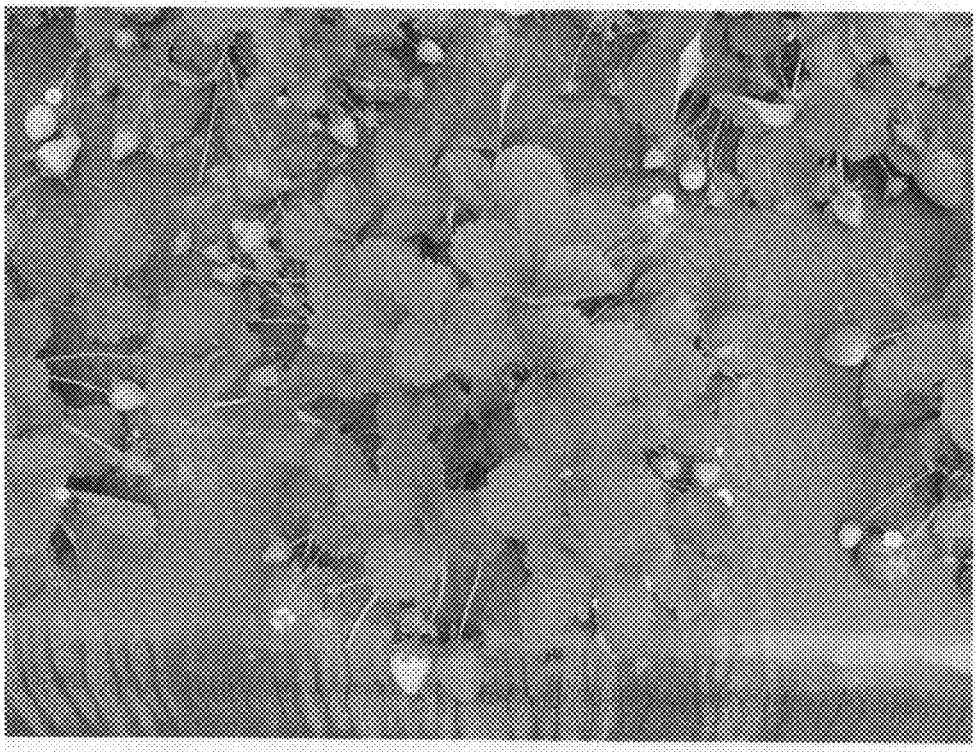
'Winter Dawn' strawberry, 3-6-02